United States Patent [19]

Bramm et al.

[11] 4,334,180
[45] Jun. 8, 1982

[54] ELECTROMAGNETIC DRIVING MECHANISM FOR OSCILLATING DISPLACEMENT PUMPS

[75] Inventors: Guenter Bramm; Pavel Novak, both of Munich, Fed. Rep. of Germany

[73] Assignee: Speidel & Keller GmbH & Co. KG, Jungingen, Fed. Rep. of Germany

[21] Appl. No.: 190,323

[22] PCT Filed: May 31, 1979

[86] PCT No.: PCT/DE79/00053
§ 371 Date: Jan. 17, 1980
§ 102(e) Date: Jan. 17, 1980

[87] PCT Pub. No.: WO79/01155
PCT Pub. Date: Dec. 27, 1979

[30] Foreign Application Priority Data

May 31, 1978 [DE] Fed. Rep. of Germany ....... 2823802

[51] Int. Cl.³ .............................................. G05B 11/00
[52] U.S. Cl. ..................................... 318/687; 318/135; 417/416; 128/1 D; 310/37
[58] Field of Search ............... 318/135, 687, 626, 627; 310/23, 34, 37; 417/416; 128/1 D

[56] References Cited

U.S. PATENT DOCUMENTS

| | | | |
|---|---|---|---|
| 2,483,895 | 10/1949 | Fisher ..................... | 318/135 |
| 3,737,883 | 6/1973 | Sordello et al. ............. | 318/687 UX |
| 4,078,198 | 3/1978 | Murakosi ..................... | 318/627 |
| 4,122,379 | 10/1978 | Richter ..................... | 318/627 |
| 4,220,899 | 9/1980 | von der Heide ............... | 318/135 |

FOREIGN PATENT DOCUMENTS

| | | |
|---|---|---|
| 2059971 | 6/1972 | Fed. Rep. of Germany . |
| 2723215 | 1/1977 | Fed. Rep. of Germany . |
| 2614973 | 10/1977 | Fed. Rep. of Germany . |
| 1091752 | 4/1955 | France . |
| 2094315 | 10/1972 | France . |
| 718199 | 12/1951 | United Kingdom . |
| 919796 | 2/1963 | United Kingdom . |

OTHER PUBLICATIONS

"Design Notes", Control and Instrumentation, Sep. 1977, vol. 9, No. 8, 318-135.
"Design Notes", Control and Instrumentation, Sep. 1977, vol. 9, No. 8, 318-135.
E & M; Elektrotechnik und Maschinenbau; by O. Roubicek "Die Uebertragungseigenschaften des Niederfrequenzsynchronlinearmotors", Jan. 1973; pp. 23 to 29.

*Primary Examiner*—B. Dobeck
*Attorney, Agent, or Firm*—W. G. Fasse; D. F. Gould

[57] ABSTRACT

Electromagnetic driving mechanism for oscillating displacement pumps (10) is described which comprises a linear motor (21, 22) and a control circuit (51, 52, 53, 54). The control circuit controls the stroke movement of the linear motor (21, 22) in response to the deviation of the actual value of a stroke parameter (stroke distance, stroke speed, stroke acceleration, and pressure of the medium being pumped) from the reference value of this stroke parameter. A preferred embodiment is assembled in such a manner that the pump (10) proper may be easily exchanged and constructed as a discardable unit. Such a pump unit (10) is particularly desirable in connection with blood pumps.

23 Claims, 7 Drawing Figures

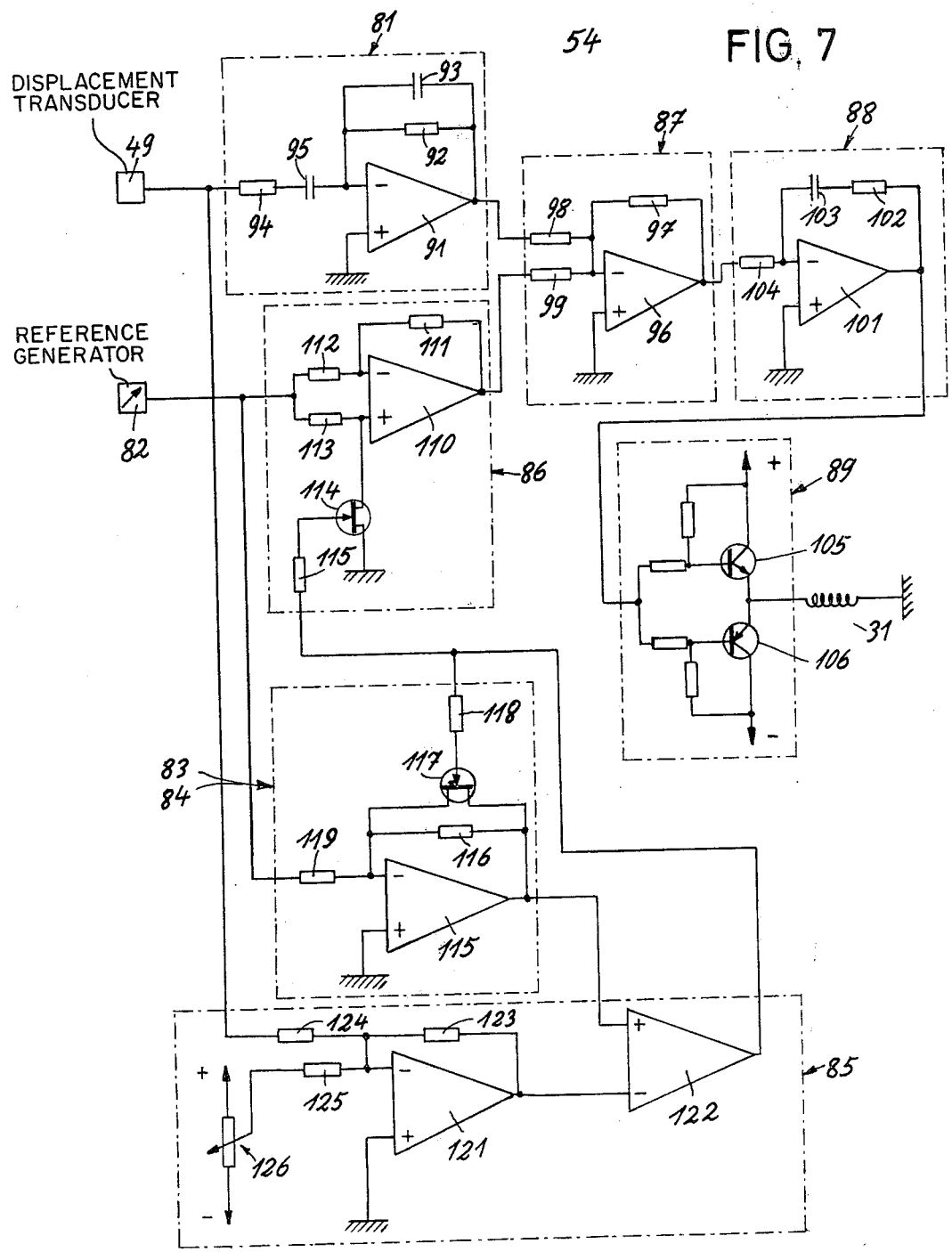

ELECTROMAGNETIC DRIVING MECHANISM FOR OSCILLATING DISPLACEMENT PUMPS

CROSS-REFERENCE TO RELATED APPLICATIONS

The present application is based on German Patent Application Ser. No. P 2,823,802.0, filed in the Federal Republic of Germany on May 31, 1978 and on the corresponding application PCT/DE79/00053 filed on May 31, 1979. The priority of the original German filing date is claimed.

BACKGROUND OF THE INVENTION

The invention relates to a driving mechanism for oscillating displacement pumps. Such driving mechanisms are known from British Pat. No. 1,442,500. In these known driving mechanisms the time sequence of the volume flow and of the suction pressure as well as of the discharge pressure is determined by the geometry of the pole shoes and of the field configuration. Thus, among others, the flow speed is also determined.

When conveying media which can withstand only a certain reduced pressure or increased pressure without damage, it is necessary to reduce the driving speed of such pumps so that the occurring reduced or increased pressures do not exceed the permissible limit values. Thus, the mass flow is substantially reduced and the pump is insufficiently utilized. However, it is possible to reduce these difficulties by using volume storage means in the form of expansion chambers arranged upstream or downstream, whereby the entire pumping system becomes more involved and more expensive. Besides, by these features it is not excluded that the permissible reduced or increased pressures are exceeded anyway. Additionally, these features cause an increase in the volume of the medium being conveyed in the pump conveying system.

In connection with media to be conveyed which may not be exposed to certain maximum shearing stresses, it is necessary to keep the acceleration forces of the moving pump components so low that the limit value of the shearing stress is not exceeded at any points of the hydraulic system. This also reduces the degree of efficiency of the pump.

It is known in connection with positioning means for disc memories in the data processing art, which comprise electro-dynamic linear motors, to provide a control circuit which controls the positioning stroke in response to the difference between the actual value of the positioning displacement and the reference value of the desired position as well as in response to the positioning speed. However, in connection with such positioning means for disc memories used in the electronic data processing art, problems of quite a different type occur. Especially, it is essential that the desired reference position is reached precisely so that this known device could not provide any hints with regard to driving mechanisms for oscillating displacement pumps ("Feinwerketechnik and Mikronik", Vol. 77, Nr.4 1973, pages 151 to 157).

OBJECTS OF THE INVENTION

Thus, it is the object of the invention to construct the above mentioned driving mechanism in such a manner that on the one hand the permissible limit values for the reduced pressure, the increased pressure, the acceleration and so forth, are maintained with certainty while on the other hand the largest possible conveying capacity is achieved within the limit values.

SUMMARY OF THE INVENTION

The invention has achieved the above objectives in an electromagnetic drive mechanism for an oscillating displacement pump, including a stator and a runner which is guided by the stator and movable across the field lines of the stator, and further including a coupling device between the stator and the runner on the one hand, and between the stator and the displacement pump on the other hand, said stator comprising a permanent magnet system for producing the stator field and said runner comprising a runner winding which is characterized by a control circuit arrangement which comprises at least one first signal pick-up for providing a signal representing the actual or measured value of a stroke parameter by at least one reference second pick-up for providing a signal representing a reference value of a stroke parameter, by at least one comparator operatively connected with its two inputs to said first and second pick-ups, and which is further characterized in that said runner winding is connected to the output of the comparator through a closed loop controller member and, if desired, through a direction reversing switch and through a power output amplifier, whereby the current in said runner winding is controlled during the movement of said runner winding when it is performing a stroke.

A driving mechanism according to the invention in which the signal pick-up is a displacement transducer, makes possible the utilization of the driven displacement pump as a dosing pump. If the signal pick-up provides a signal which depends on the speed for example in a transducer followed by a differentiating circuit or speed transducer, the driven displacement pump is especially suitable for conveying of media, such as blood, which are sensitive relative to high shearing stresses. If the signal pick-up is a pressure transducer, it is possible to avoid exceeding a predetermined excess pressure and/or to avoid that the pressure falls below a predetermined reduced pressure. Thus, the driven displacement pump is especially suitable for pressure sensitive media or for media which tend to degas. If the reference value pick-up e.g. 2 speed pick-up is connected to two end position value pick-ups for the two reversing circuits of the runner, it is possible to keep the pump frequency constant while the conveying speed is variable. This feature is especially advantageous for using the driven pump as a blood pump.

If the runner is guided along the pole core of a correspondingly shaped stator, a rather simple longitudinal guiding of the runner is accomplished which uses components which are present anyway. If this guiding means is constructed with anti-friction bearings, a low friction guiding is accomplished which thus has a low dissipation loss.

The assembly of the mechanism results in a very compact unit comprising the driving mechanism and the displacement pump. The present coupling mechanism according between the motor and the pump provides an especially stiff coupling device having a high strength and an efficient material utilization of the components. Further, the assembly of the displacement pump with its drive means is much simplified and so is its maintenance. Besides, in this way it is possible to exchange the same parts for one another. The present displacement pump with its drive is useful for many purposes for example for conveying, especially difficult media such as strongly adhesive media or media which are aggressive relative to conventional sealing means or media which are sensitive relative to the sealing means. The present pump may be manufactured relatively cheaply of a material suitable for many purposes. Where it is difficult to remove media or where high requirements regarding the cleanliness of the pump component must be satisfied, for example, germ-free requirements when the pump is used as a blood pump, the pump component may be treated as a disposable part without any substantial costs. In an embodiment of the driving mechanism and of the displacement pump according to certain aspects of the invention it is easy to assemble the two pump components and to also disassemble the pump components again. Thus, treating the pump component as a disposable part is possible.

BRIEF FIGURE DESCRIPTION

The invention will be explained in the following with reference to an example embodiment shown in the drawings of a driving unit with an oscillating displacement pump and with reference to several control circuits for the driving unit, wherein:

FIG. 7 is a circuit arrangement of the block schematic according to FIG. 6.

DETAILED DESCRIPTION OF PREFERRED EXAMPLE EMBODIMENTS AND OF THE BEST MODE OF THE INVENTION

Figure 1:
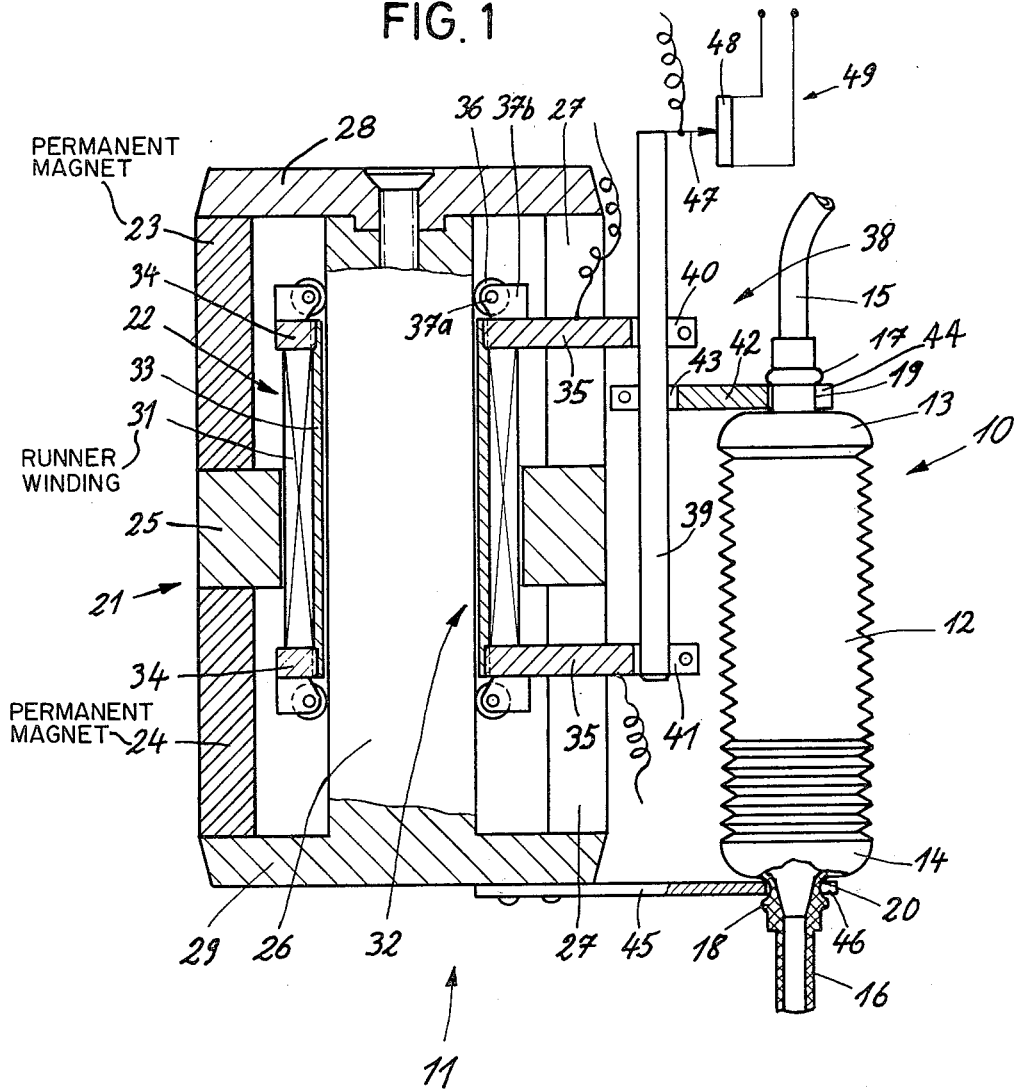
FIG. 1 shows a partially schematic vertical section through a driving mechanism and a bellows pump according to section line I—I in FIG. 2.
Figure 2:
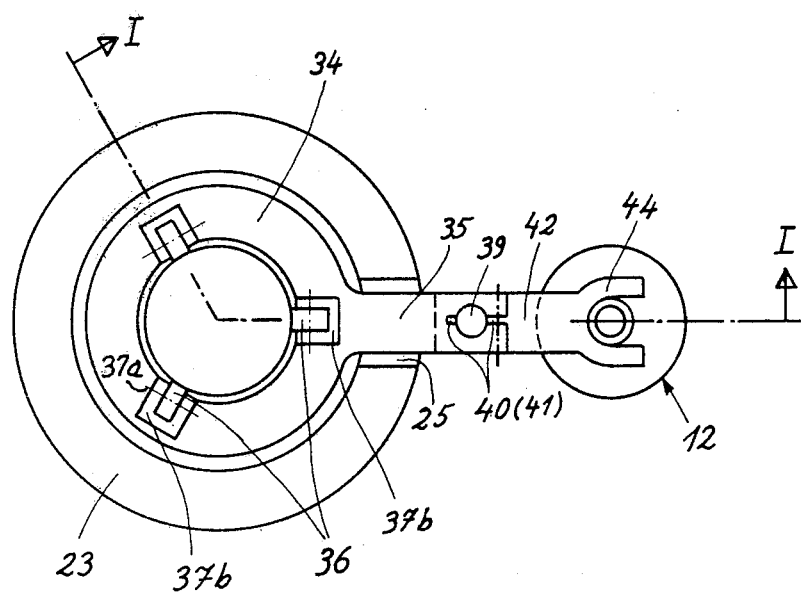
FIG. 2 is a top plan view onto the mechanism according to FIG. 1, with the upper yoke disc removed.

The oscillating displacement pump shown in FIGS. 1 and 2 comprises a bellows pump 10 and an electromagnetic driving mechanism 11 forming main structural groups.

The bellows pump 10 is constructed as a pump with an internal throughflow. The pump comprises a folding bellows having a cylindrical shape which merges at both of its facing ends into a respective smooth, vaulted annular cover member 13 or 14. In the center of the cover members 13 and 14 there is joined without any seam a hose member 15 or 16. At the transition between the cover member 13 and 14 and the respective hose member 15 and 16 there is an annular bulge 17 or 18 which extends in the radial direction beyond the axially adjacent members. Thus, a ring groove 19 or 20 is formed between the ring bulge 17 and 18 and the respective cover member 13 or 14.

The folding bellows 12, the two cover members 13 and 14, the adjacent, connected hose members 15 and 16, and the ring bulges 17 and 18 are formed as a single piece of a rubber elastic material, for example, of polyethylene or polyvinylchloride.

The valves necessary for a continuous conveying of a medium through the pump are not shown in FIG. 1. These valves may be constructed either as passive valves, for example, as spring loaded check valves which may be connected by means of hose nipples to the hose members 15 and 16 and which are operated by the flowing medium itself, or these valves may be constructed as active valves, for example, as electromagnetically operated hose valves which are arranged outside the hose members 15 and 16 and which are externally effective on the hose members as so-called pinch cocks or pinch valves.

The electromagnetic driving mechanism 11 comprises a stator 21 and a runner 22. The stator comprises two permanent magnet systems 23 and 24 for producing the magnetic stator field. Both permanent magnet systems are constructed as hollow cylinder shapes as shown in FIG. 2. The two permanent magnet systems 23 and 24 are made of an aluminum nickel cobalt alloy. The ring shape of the hollow cylinder of the permanent magnet system 23 and 24 is interrupted on the right-hand side in FIGS. 1 and 2 by a respective opening 27 extending through in the radial and axial direction. The opening 27 is bounded by plane wall surfaces arranged in parallel relative to each other.

The magnetic fields of the two permanent magnet systems 23 and 24 are aligned to oppose each other.

A circular, ring shaped pole shoe 25 is located between the two permanent magnet systems 23 and 24. The permanent magnet systems 23 and 24 abut on the axial facing surfaces of the pole 25. A cylindrical pole core 26 having a circular cross-section is arranged centrally within the pole shoe 25 and the permanent magnet systems 23 and 24. A ring shaped pole gap of uniform gap width is provided between the ring shaped pole shoe 25 and the cylindrical pole core 26. The pole core 26 has the same axial length as the sum of the axial extensions of the pole shoe 25 and of the two permanent magnet systems 23 and 24. A circular yoke disc 28 or 29 is located at each of the two ends of the pole core. The yoke disc 28 located at the top in FIG. 1 is formed as an individual component which is screwed to the pole core 26. The lower yoke disc 29 forms an integral part with the pole core 26. It may also be contemplated that both pole discs are made as individual components and screwed to the pole core or that the pole core is divided about at its longitudinal center and that the pole discs are formed as an integral part at each end of the pole core.

The ring shaped pole shoe 25, the pole core 26, and the two yoke discs 28 and 29 are made of a soft magnetic, ferro-magnetic material, for example, of an iron cobalt alloy. The axial extension of the pole shoe 25 and of the pole core 26 are adjusted relative to each other and relative to the axial extension of the two permanent magnet systems 23 and 24 in such a manner that in the assembled condition of these parts there is no air gap between the parts.

The runner 22 is made as a non-ferro-magnetic body which comprises a winding 31 and a winding carrier 32. The winding carrier 32 is made of a sleeve 33 and of two end discs 34. The sleeve 33 has the shape of a thin hollow cylinder. The two end discs 34 have a circular ring shape and a radially outwardly extending extension, each of which forms a cantilever arm 35 of the runner 22.

The axial extension of the pole shoe 25, of the stator 21, and the axial extension of the winding 31 of the runner 22 as well as the largest stroke of the runner 22 that may occur in operation, and thus the bellows pump 10 are so adjusted relative to one another that the axial extension or length of the winding 31 is at least approximately equal to the sum of the axial extension or length of the pole shoe 25 and of the largest possible operational stroke of the runners 22. The largest operational stroke is, as a rule, predetermined by the requirements to be satisfied by the bellows pump 10. The axial length or extension of the pole shoe 25 results primarily from the magnetic characteristics of the components participating in the generation of the stator field, whereby the axial length of the windings 31 is then also determined. Due to this dimensioning, all turns of the winding 31 dip at least once into the radial stator field in the pole gap between the pole shoe 25 and the pole core 26 when the runner 22 executes a full stroke. None of the turns runs along completely idle without ever participating in the power generation of the driving mechanism 11 and without merely causing energy losses.

The runner 22 is guided along the pole core 26 by means of two groups of anti-friction bearings 36, whereby each group comprises three anti-friction bearings 36 which are uniformly distributed about the circumference of the runner 22 as shown in FIG. 2. One anti-friction bearing group is arranged at each one of the facing sides of the winding carrier 32. The inner races of the anti-friction bearings 36 are located on bearing pins 37a which in turn are inserted in small bearing bucks 37b. These bearing bucks 37b are screwed down on the outwardly facing facing ends of the two end discs 34 by means of screws not shown. The outer races of the anti-friction bearings 36 run directly on the circumferential surface of the pole core 26. The cantilever arms 35 are part of a coupling device 38 between the bellows pump 10 and its driving mechanism 11. A bail 39 forms a further part of the coupling device 38 and is constructed as a cylindrical rod having a circular cross-section. This rod shaped bail 39 is inserted into a respective circular through hole in the cantilever arms 35, wherein it is respectively clamped tight by means of a respective radially extending clamping slot 40 or 41 and a clamping screw not shown, but screwed-in in the circumferential direction. A connecting plate 42 is clamped to the bail 39 as a further part of the coupling device 38 again by means of a clamping slot 43 and a clamping screw not shown. Thus, the connecting plate 42 may easily be adjusted on the bail 39 with reference to the dimensions of the pump bellows 12 and relative to the expansion condition of the latter in the starting position of the runner 22 of the driving mechanism 11. The connecting plate 42 comprises at its end facing away from the bail 39 a fork end 44. This fork end 44 is adjusted in its dimensions to the dimensions of the ring groove 19 at the upper end of the folding bellows 12 in FIG. 1. A second connecting plate 45 forms a further component of the coupling device 38 and is screwed to the yoke disc 29 located at the lower end. The connecting plate 45 also has a forked end 46 facing away from the yoke disc 29. The forked end 46 is also adjusted, just as the forked end 44 of the connecting plate 42, to the dimensions of the ring groove 20 at the lower end of the folding bellows 12.

As indicated in FIG. 2 and as more clearly seen in FIG. 1, the folding bellows 12 of the bellows pump 10 is assembled with the driving mechanism 11 in such a manner that the forked end 44 of the connecting plate 42 engages into the ring groove 19 at the upper end of the folding bellows 12 and the forked end 46 of the connecting plate 45 engages in the ring groove 20 at the lower end of the folding bellows 12. The coupling device 38 transmits the stroke movements of the parts of the driving mechanism 11 which are movable relative to each other, to the bellows pump 10. This is so because of the axial engagement of the forked end 44 of the connecting plate 42 and the parts of the folding bellows 12 on both sides of the ring groove 19, namely, the cover member 13 and the ring bulge 17, and because of the axial engagement of the forked end 46 of the connecting plate 45 with the parts of the folding bellows 12 adjacent to the ring groove 20, namely, the cover member 14 and the ring bulge 18.

As may be seen from FIG. 1, the rod shaped bail 39 extends upwardly beyond the cantilever arm 36. A sliding spring 47 is secured to this upwardly extending end. The sliding spring 47 rests against a sliding resistor 48 and slides back and forth on the sliding resistor in response to the stroke movement of the bail 39. The sliding resistor 48 is secured in a manner not shown, in a fixed position relative to the stator 21 of the driving mechanism 11. The sliding spring 47 and the sliding resistor 48 form a signal pick-up, namely, a displacement transducer 49 forming part of a control circuit arrangement 51, 52, 53 or 54 which will be explained in the following with reference to FIGS. 3 to 6.

Figure 3:
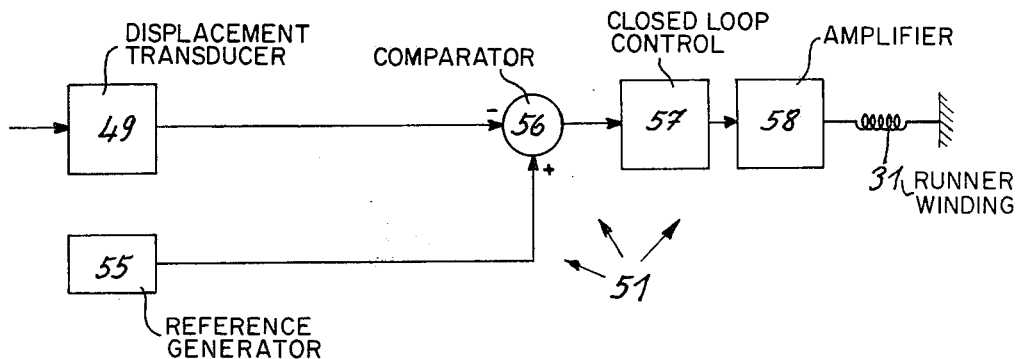

The control circuit arrangement 51 shown in FIG. 3 serves as a displacement or stroke control of the driving mechanism 11 and thus of the bellows pump 10.

The control circuit arrangement 51 shown in FIG. 3 comprises in addition to the displacement transducer 49, a reference value pick-up or generator 55 for the reference displacement of the runner 22, a comparator 56, a closed loop control member 57 including a proportional integration controller and a power output amplifier stage 58. The rated or reference value generator 55 produces a displacement time signal and the runner 22 is intended to follow with its stroke movement, said displacement time signal. The output of the displacement transducer 49 and of the reference value generator 55 are connected to the two inputs of the comparator, however, with signs (polarities) opposing each other. The comparator forms a sum representing signal from the two input signals. The output of the comparator 56 is connected to the input of the closed loop controller and the output of the latter is connected to the input of the power output amplifier 58. The power output amplifier provides an adjustment signal to the winding 31 of the runner 22 connected to the output of the power output amplifier.

Figure 4:
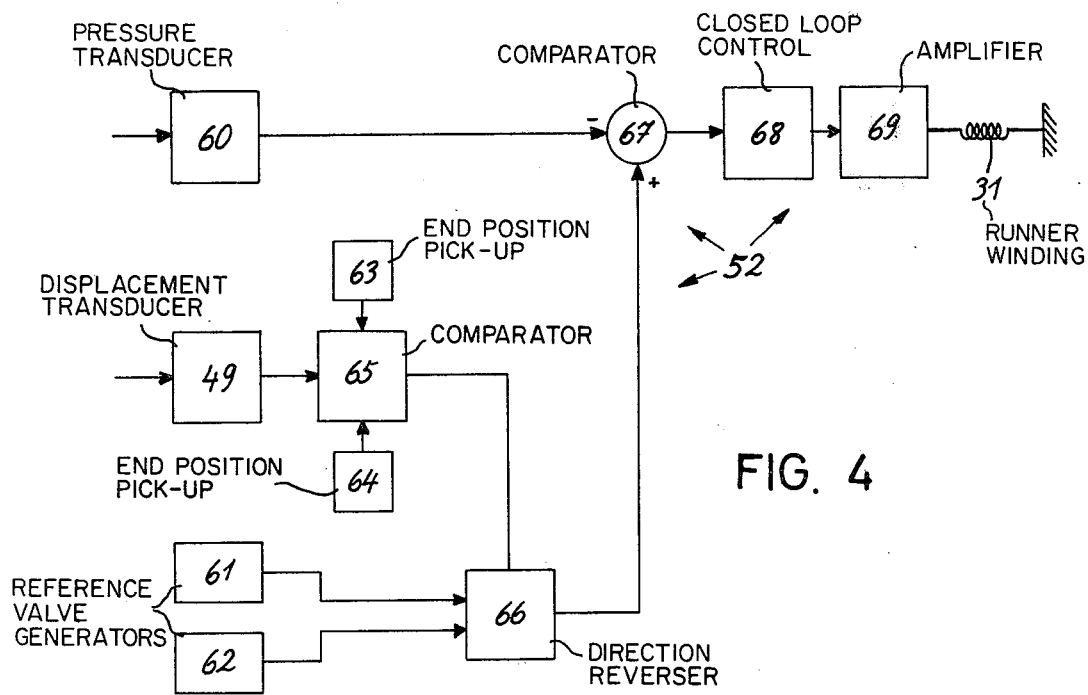
FIGS. 3 to 6 illustrate block circuit diagrams of different control circuits for the mechanism according to FIGS. 1 and 2.

The control circuit 52 shown in FIG. 4 serves for controlling the pressure in closed loop fashion in the bellows pump 10 and/or in the connected hydraulic system. The control circuit 52 comprises in addition to the displacement transducer 49 a pressure transducer 60, one each of a reference value generator 61 or 62 for the rated pressure at each of the two movement directions of the runner 22, one each of an end position value pick-up 63 or 64 for the two reversing positions of the runner 22 and a comparator 65. The control circuit 52 further comprises a direction reversing switch 66, a second comparator member 67, and a closed loop control member 68 including a proportional integration controller and an output power amplifier stage 69 as described above.

The output of the displacement transducer 49 is connected to the signal conductor input of the comparator 65. In addition, the output of each of the two end position value pick-ups 63 and 64 is connected to the control conductor inputs of the comparator 65. The output of the comparator 65 is connected to the control input of the direction reversing switch 66. The outputs of the two reference value generators 61 and 62 are connected to the signal conductor inputs of the direction reversing switch 66. The output of the latter and the output of the pressure transducer 60 are connected, with opposite signs (polarities) to the two inputs of the further comparator member 67. The output of the further comparator member 67 is in turn connected to the input of the closed loop control member 68 and the output of the latter in turn is connected to the input of the power output amplifier stage 69 which also provides a control signal to the winding 31 of the runner 22.

Figure 5:
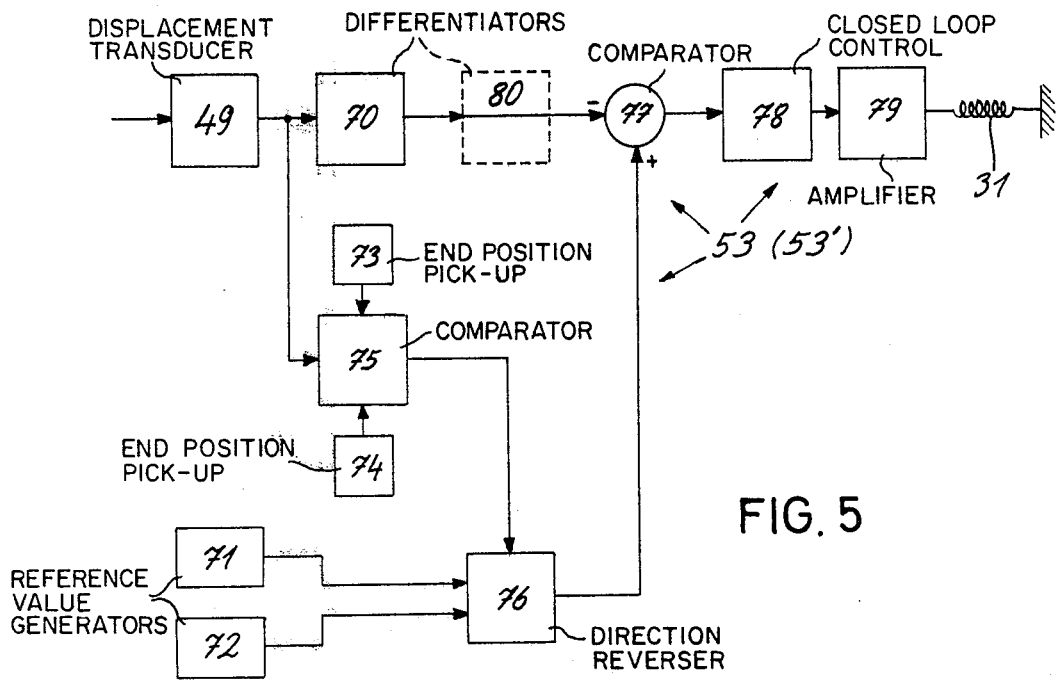

The control circuit 53 shown in FIG. 5 serves for the closed loop speed control of the driving mechanism 11. With a supplementing feature this control circuit 53 also serves for the closed loop acceleration control of the driving mechanism 11.

The control circuit 53 comprises in addition to the displacement transducer 49 a differentiating circuit 70, one each of a reference value generator 71 or 72 for the reference or rated speed in each of the movement directions of the runner 22, one each of an end position value pick-up 73 or 74 for the two reversing positions of the runner 22, a comparator 75, a direction reversing switch 76, a comparator member 77, a closed loop control member 78 with a proportional integration controller, and a power output amplifier stage 79. The output of the displacement transducer 49 is connected to the input of the differentiating circuit 70 and to the signal conductor input of the comparator 75. The output of each of the two end position value pick-ups 73 and 74 is connected to the control conductor inputs of the comparator 75. The output of the latter is connected to the control conductor input of the direction reversing switch 76. The outputs of the reference or rated value pick-up 71 and 72 are connected to the signal conductor inputs of the direction reversing switch 76. The signal conductor outputs of the latter, as well as the output of the differentiating circuit 70 are connected, with opposite signs (polarities) to the inputs of the comparator member 77. The output of the latter is connected to the input of the closed loop control member 78 and the output of the latter is connected to the input of the power output amplifier stage 79. The latter supplies the winding 31 of the runner 22 with a control signal required for the closed loop speed control or regulation.

If in the control circuit arrangement 53 described above a second differentiating member 80 is connected between the differentiating member 70 and the comparator members 77, the output signal of the second differentiating member 80 corresponds to the second differentiation of the displacement signal relative to time. Thus, this signal corresponds to the measured signal of the acceleration of the runner 22 of the driving mechanism 11. If the two rated value pick-up or generators 71 and 22 are adjusted so that each delivers a respective rated value signal for the acceleration in one of the two motion directions of the runner 22, the thus modified circuit arrangement 53' operates as a closed loop control circuit for the acceleration of the driving mechanism 11.

Figure 6:
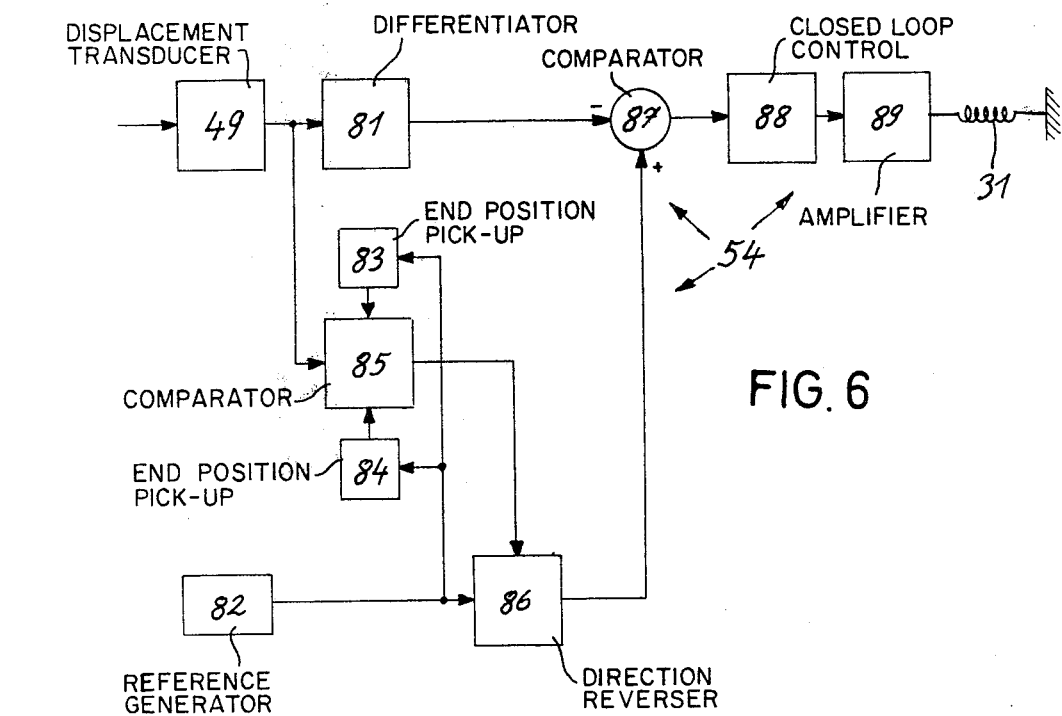

The control circuit arrangement 54 shown in FIG. 6 serves for the closed loop control and thus for the maintaining of a constant stroke frequency of the bellows pump 10 and of its driving mechanism 11 while the stroke speed is varying. The control circuit 54 comprises in addition to the displacement transducer 49 a differentiating circuit 81, a rated value generator 82 for the rated or reference speed in the two directions of motions of the runner 22. The control circuit 54 further comprises an end position value pick-up or transducer 83 or 84 for each of the two reversing positions of the runner 22, a comparator 85, a direction reversing switch 86, a comparator member 87, a closed loop control member 88 including a proportional integration controller, and a power output amplifier stage 89. The output of the displacement transducer 49 is connected to the input of the differentiating circuit 81 and simultaneously to the signal conductor input of the comparator 85. The output of the reference or rated value pick-up or generator 82 is connected on the one hand to the signal conductors input of the direction reversing switch 86 and on the other hand to each of a control conductor inputs of each of the two end position value pick-ups 83 and 84. The output of the latter is connected to each of the control conductor inputs of the comparator 85. The outputs of the latter is connected to the control conductor input of the direction reversing switch 86. The signal conductor output of the switch 86 and the output of the differentiating circuit 81 are in turn connected, with opposite signs (polarities) to the inputs of the comparator circuit 87. The output of the latter is connected to the input of the control member 88 and the output of the control member 88 is connected to the power output stage 89 which supplies the winding 31 of the runner 22. Due to supplying the output signals of the speed reference value 82 also to the control conductor inputs of the end position value pick-ups 83 and 84, the end position limiting values of the stroke are respectively displaced in response to a change in the stroke speed of the driving mechanism which may occur for any reason. Thus, a longer stroke is performed when the stroke speed is higher and vice versa. As a result, the stroke frequency of the entire oscillating system remains constant within certain limits of the stroke and thus of the speed.

For elucidating the circuit diagrams of one of the control circuits 51 to 54 the circuit diagram of the last discussed control circuit 54 is explained in more detail with reference to FIG. 7.

The differentiating circuit 81 comprises an operational amplifier 91 including a resistor 92 and a capacitor 93 in a negative feedback circuit. The resistor 92 and the capacitor 93 are connected in parallel to one another. A series circuit comprising a resistor 94 and a capacitor 95 is connected to the negative input of the operational amplifier 91. Due to the resistor 92 in the negative feedback circuit and due to the capacitor 95 in the input circuit, the operational amplifier 91 acts as a differentiating circuit. The resistor 94 and the capacitor 93 cooperate with the operational amplifier as a low pass filter.

The comparing circuit 87 comprises an operational amplifier 96 with a resistor 97 forming a negative feedback circuit. The negative input of the operational amplifier 96 is connected to two resistors 98 and 99 connected in parallel to each other. The signal conductor output of the differentiating circuit 81 is connected to the resistor 98 and the signal conductor output of the direction reversing switch 86 is connected to the resistor 99. Thus, the comparator provides a sum signal based on the two input signals.

The control member 88 comprises an operational amplifier 101 including a negative feedback circuit comprising a resistor 102 and a capacitor 103 connected in series. The negative input of the operational amplifier 101 is further connected to a resistor 104 which in turn is connected to the output of the comparing circuit 87. Due to this circuit arrangement, the operational amplifier 101 has simultaneously a proportional as well as an integrating transmission function or characteristic.

The power output stage 89 comprises two complementary transistors 105 and 106 which operate as a push-pull current amplifier in the A–B type of operation.

The direction reversing switch 86 comprises an operational amplifier 110 with a negative feedback circuit including a resistor 111. The negative input is further connected to a resistor 112. The positive input is connected to a resistor 113. The positive input of the operational amplifier 110 is further connected to the drain terminal of a field effect transistor (FET) 114. The source terminal of the field effect transistor 114 is connected to ground. The gate electrode of the field effect transistor 114 forms with the series resistor 115 the control conductor input of the direction reversing switch 86. The output of the comparator 85 is connected to the just mentioned control conductor input of the direction reversing switch 86. Depending upon the output voltage of the comparator 85, the reference value of the speed appears at the output of the direction reversing switch with a positive or a negative polarity.

The end position pick-up 83, 84 comprises an operational amplifier 115' including a negative feedback circuit with a resistor 116 connected in parallel to a field effect transistor 117. The gate electrode of the field effect transistor 117 is connected through a series resistor 118 to the output voltage of the comparator 85. The negative input of the operational amplifier 115' is further connected to a resistor 119 which in turn is connected to the output of the reference value pick-up or generator 82 for the speed. Depending on the output voltage of the comparator 85, one or the other end position value of the displacement transducer 49 appears at the output of the end position value pick-ups or generators 83, 84. In this context, the end position value is proportional to the reference speed due to the connection of the reference value pick-up or generator 84 for the speed to the resistor 119 and to the control conductor input of the end position value pick-up or generator 83, 84.

The comparator 85 comprises two operational amplifiers 121 and 122. The operational amplifier 121 comprises in its negative feedback circuit a resistor 123. A resistor 124 is connected to the negative input of the operational amplifier 121. The resistor 124 forms the signal conductor input of the comparator 85 and the output of the displacement transducer 49 is connected to this signal conductor input of the comparator 85. Additionally, a resistor 125 is connected to the negative input of the operational amplifier 121 and to a voltage divider 126. The output of the first operational amplifier 121 is connected to the negative input of the second operational amplifier 122, the positive input of which forms the control conductor input of the comparator 85 and is connected to the outputs of the end position value pick-up or generator 83, 84. Due to the circuit arrangement of the first operational amplifier 121, the latter supplies a sum signal representing the output signal of the displacement transducer 49 and the output value of the voltage divider 126, to the second operational amplifier 122. The second operational amplifier 122 constitutes the comparator portion proper and supplies a direction dependent control signal. The starting position for the stroke movement of the runner 22 may be adjusted at the voltage divider 126 at the negative input of the first operational amplifier 121.

As far as nothing else has been said above, it is to be assumed that the positive input of the described operational amplifiers is connected to ground.

We claim:

1. An electromagnetic drive mechanism for providing a controlled back and forth driving movement, comprising stator means including magnet means for providing respective stator magnetic fields, runner means, support means supporting said runner means for a linear back and forth displacement relative to said stator magnetic fields, runner winding means (31) operatively carried by said runner means, whereby said runner winding means interact with said stator magnetic fields during the movement of said runner means, a closed loop control circuit operatively connected to said runner winding means for controlling said driving movement, said closed loop control circuit comprising sensing means for sensing an instantaneous measured value to provide a corresponding first electrical signal representing an instantaneous parameter of said runner means, reference signal means for providing a second electrical signal representing a rated value, comparator means having a first input connected to said sensing means and a second input connected to said reference signal means for comparing said first and second electrical signals with each other, and control circuit means connecting an output of said comparator means to said runner winding means for supplying a comparator output control signal to said runner winding means whereby the control of said runner means takes place during any displacement driving and within said back and forth movement.

2. The mechanism of claim 1, further comprising oscillating pump means, connecting means for securing said oscillating pump means to said runner means, end position sensing means connected to said closed loop control circuit for sensing return point positions of said runner means to provide respective electrical return signals to said closed loop control circuit, and direction reversing switch means also connected to said closed loop control circuit for reversing the direction of displacement of said runner means.

3. The mechanism of claim 2, comprising further comparator means having three inputs, said sensing means having an output connected to said first mentioned comparator means and to one input of said further comparator means, said end position sensing means comprising two sensors connected to the respective other inputs of said further comparator means, said direction reversing switch means being connected to an output of said further comparator means to said reference signal means and to said first mentioned comparator means for providing said control signal for said runner means.

4. The mechanism of claim 3, wherein said reference signal means comprise two reference signal sources both of which are operatively connected to said direction reversing switch means for providing a reference signal for each direction of movement of said runner means.

5. The mechanism of claim 3, further comprising electrical conductor means operatively connecting said reference signal means to both of said end position sensors and to said direction reversing switch means.

6. The mechanism of claim 1, wherein said sensing means for sensing an instantaneous measured value comprise displacement sensing means for measuring an electrical signal corresponding to the instantaneous displacement or distance travelled by said runner means.

7. The mechanism of claim 6, wherein said displacement sensing means comprises a potentiometer resistor (48) and a sliding spring contact (47) connected to said runner means for adjusting said sliding spring contact along said potentiometer resistor (48).

8. The mechanism of claim 6 or 7, further comprising differentiating circuit means (70, 81) operatively connected between the displacement sensing means (49) and said comparator means (77) for providing a signal representing the instantaneous speed of said runner means.

9. The mechanism of claim 8, wherein said differentiating circuit means comprise two differentiating members (70, 80) connected in series between the displacement sensing means and the comparator means (77) for providing a signal representing the acceleration of said runner means.

10. The mechanism of claim 1, wherein said sensing means for sensing an instantaneous measured value comprise a pressure transducer (60) connected to said comparator means.

11. The mechanism of claim 1, wherein said sensing means for sensing an instantaneous measured value connected to said comparator means is a velocity sensor.

12. The mechanism of claim 1, wherein said control circuit means in said closed loop control circuit comprise an integral controller member for integrating a control signal.

13. The mechanism of claim 1, wherein said control circuit means in said closed loop control circuit comprise a proportional integral control member for proportionally integrating a control signal.

14. The mechanism of claim 1, wherein said control circuit means in said closed loop control circuit comprise a proportional integral differential control member for proportionally integrating and differentially a control signal.

15. The mechanism of claim 1, wherein said stator means comprise an annular, closed pole shoe and a pole core arranged centrally therein, said support means of said runner means (22) comprising guide means for guiding the runner means along the pole core (26).

16. The mechanism of claim 15, wherein said runner guide means comprise two groups of guide members each group comprising three anti-friction bearings (36), one each of the anti-friction bearing groups being arranged at each end of the runner means so that said anti-friction bearings (36) run directly on the pole core (26).

17. The mechanism of claim 15 or 16, wherein said magnet means of said stator means comprise two permanent magnet systems including hollow cylinders with aligned slots, said mechanism further comprising cantilever arm means (35) connected with said runner means (22), said cantilever arm means extending at right angles to the movement path of said runner means (22) and through said slots (27) aligned in parallel to said movement path of the runner means (22), said cantilever arm means (35) being connectable to a movable member (13) to be driven.

18. The mechanism of claim 17, wherein said cantilever arm means comprise two cantilever arms (35), each of which is rigidly connected substantially to a respective end of said runner means (22) and each of which extends through a respective one of said slots of the adjacent permanent magnet system cylinders (23, 24), said runner means further comprising a rod (39) for rigidly connecting both cantilever arms (35) to each other outside said stator means (21), said rod (39) in turn being connectable with a movable member to be driven.

19. The mechanism of claim 1, further comprising pump means and plug-in type connection means operatively arranged between said pump means and said mechanism, said pump means comprising a stationary part connected to said stator means and a movable part connected to said runner means for operating said pump means by the movement of said runner means.

20. The mechanism of claim 19, wherein said pump means comprise a bellows pump (10) having a stationary end connected to said stator means and a movable end connected to said runner means.

21. The mechanism of claim 20, wherein said bellows pump (10) comprises at each of its two ends (13, 14) a reduced diameter portion (19, 20) between two larger diameter portions (13, 17, 14, 18) extending in both axial directions from the respective reduced diameter portions.

22. The mechanism of claim 21, wherein the reduced diameter portion is constructed as an all around groove (19, 20) and the adjacent larger diameter portions are constructed as all around bulges (17, 18).

23. The mechanism of claim 19, wherein said plug-in type connection means (42, 45) each comprise a fork type end (44, 46) for holding said pump means.

* * * * *